Figure 1:
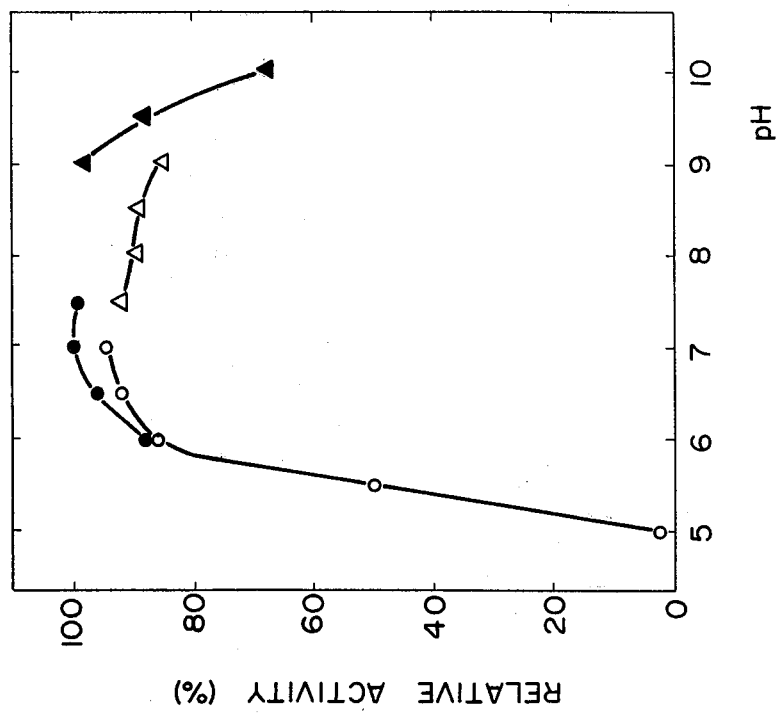

United States Patent [19]

Ikuta et al.

[11] 4,420,562
[45] Dec. 13, 1983

[54] METHOD FOR PRODUCING CREATINASE

[75] Inventors: Shigeru Ikuta; Kazuo Matsuura; Hideo Misaki, all of Shizuoka, Japan

[73] Assignee: Toyo Jozo Company, Ltd., Tokyo, Japan

[21] Appl. No.: 371,458

[22] Filed: Apr. 23, 1982

Related U.S. Application Data

[63] Continuation-in-part of Ser. No. 338,607, Jan. 11, 1982, abandoned, which is a continuation-in-part of Ser. No. 158,800, Jun. 12, 1980, abandoned.

[30] Foreign Application Priority Data

Jul. 4, 1979 [JP] Japan .................................. 54-85260

[51] Int. Cl.$^3$ ........................... C12N 9/78; C12R 1/07
[52] U.S. Cl. .................................... 435/227; 435/815; 435/832
[58] Field of Search ................................ 435/227, 221

[56] References Cited

U.S. PATENT DOCUMENTS

| | | | |
|---|---|---|---|
| 3,907,644 | 9/1975 | Mollering et al. | 435/227 X |
| 4,039,384 | 8/1977 | Suzuki et al. | 435/227 |
| 4,216,292 | 8/1980 | Ikuta et al. | 435/191 |

Primary Examiner—Lionel M. Shapiro
Attorney, Agent, or Firm—Wyatt, Gerber, Shoup, Scobey & Badie

[57] ABSTRACT

Isolation method of creatinase is disclosed. The method comprises culturing a microorganism belonging to Bacillus, for example, B-0618 strain (deposition No. FERM-P 4049 at Fermentation Research Institute, Agency of Industrial Science and Technology, Japan) to obtain cells from the cultured product, obtaining sarcosine oxidase and creatinase-containing solution, fractionally eluting sarcosine oxidase and creatinase by anion exchange chromatography to obtain a creatinase fraction and then collecting creatinase.

3 Claims, 4 Drawing Figures

METHOD FOR PRODUCING CREATINASE

This application is a continuation-in-part application of application Ser. No. 338,607 filed on Jan. 11, 1982, abandoned which is a continuation-in-part application of Ser. No. 158,800, filed June 12, 1980, now abandoned.

The present invention pertains to the method for producing and isolating creatinase.

Creatinase is an enzyme classified as creatine amidinohydrolase with the enzyme number of 3.5.3.3., catalyzing the reaction represented by the following formula.

Creatine + $H_2O$ → urea + sarcosine

The production of the enzyme has so far been confined to microorganisms belonging to the genera Pseudomonas, Flavobacterium, etc.

It has now been found that a microorganism, B-0618 strain, belonging to the genus Bacillus, which was isolated from a soil sample taken from an egg-plant farm in Shimosasaki, Fukuchiyama City, Kyoto Prefecture, Japan, is capable of producing cellular creatinase from which it can be isolated successfully, when the strain is cultured in a medium containing a large amount of creatine.

The characteristics of the culture of the B-0618 strain on various culture media, according to the observations with naked eye and microscope, are described in detail in U.S. Pat. No. 4,216,292. The sarcosine oxidase and creatinase-producing B-0618 strain was named Bacillus, sp. B-0618, deposited with the Fermentation Research Institute, Agency of Industrial Science and Technology, Japan, and assigned the number, FERM-P No. 4049.

The present invention relates to a method for producing and isolating creatinase which comprises culturing Bacillus sp. B-0618, FERM-P No. 4049 which is a sarcosine oxidase and creatinase-producing strain of the genus Bacillus in a culture medium, obtaining cells from the cultured product, disrupting the a sarcosine oxidase and creatinase-containing solution, and subjecting the solution to fractional elution by anion exchange chromatography to obtain a creatinase fraction and collecting creatinase.

More particularly, the present invention relates producing and isolating creatinase which comprises subjecting the sarcosine oxidase and creatinase-containing solution obtained above to elution by concentration gradient of KCl 0.1 M to 0.5 M solutions by anion exchange chromatography, e.g., diethylaminoethyl cellulose to recover the fraction eluted at KCl 0.3 M concentration and collecting creatinase.

The microorganism employed in the present invention, mention may be made of Bacillus sp. B-0618 strain as described above. Variants may be produced naturally or artificially. Any of such variants may be employed in the present invention so long as they retain the capability of producing creatinase.

In practicing the present invention, the Bacillus sp. B-0618 is cultivated according to the conventional procedure for producing antibiotics, enzymes, etc. The type of the cultivation may be either liquid or of solid. From the industrial point view, however, it is advantageous that cells of the present strain is inoculated to a industrial scale culture medium, to effect submerged cultivation under aeration-agitation.

Conventional nutrient sources may be utilized. Typical nitrogen compounds which may be used as the nitrogen source include corn steep liquor, soybean powder, peptone, various meat extracts, yeast extract, ammonium sulfate, ammonium chloride, and the like. Useful compounds which may be used as the carbon source include glucose, molasses, glycerol, starch hydrolyzate, and the like. If necessary, salts, such as sodium chloride, potassium chloride, magnesium sulfate, potassium dihydrogen phosophate, potassium monohydrogen phosphate, and the like, may also be added. In order to produce creatinase, it is necessary that creatine be present in the culture medium. When the culture medium contains a small amount of creatine, sarcosine oxidase is predominantly produced, but when the culture medium contains a large amount of creatine, creatinase is predominantly produced. It is, therefore, preferable that creatine be added to the culture medium in order to increase the creatinase production during the cultivation. The preferred amount of creatine to be added ranges approximately from 1.5 to 2%, thereby a remarkably high yield of creatinase can be obtained.

The cultivation temperature may be suitably selected within the temperature range where creatinase is produced, but a temperature of from 26° to 33° C. is particularly advantageous. The period of the cultivation varies depending upon the various conditions, but 15 to 25 hours cultivation is ordinarily sufficient. The cultivation may be terminated when the potency of creatinase activity reaches the maximum. Creatinase and sarcosine oxidase are contained or accumulated in the cells in the cultivated product thus obtained.

The method of obtaining crude sarcosine oxidase and creatinase solution through extraction or elution of sarcosine oxidase and creatinase from the cultivated product, is exemplified hereunder. The cultivated product is subjected to solid-liquid separation, and the resulting wet cells are suspended in a phosphate buffer or Tris-HCl buffer, according to chice. Then, sarcosine oxidase and creatinase are extracted from the cells according to suitably selected or combined processes for enzyme extraction from cells, such as lysozyme processing, supersonic processing, French press processing, etc., to obtain a crude sarcosine oxidase and creatinase containing solution solution.

Purified creatinase may be obtained from the crude sarcosine oxidase and creatinase solution by conventional purification processes utilized for proteins and enzymes. For instance, the crude sarcosine oxidase and creatinase solution may be mixed with an aqueous protamine sulfate solution to remove nucleic acids, and then mixed with an organic solvent, such as acetone, methanol, ethanol, isopropanol, etc., for fractional precipitation, or with a similar salt such as ammonium sulfate, for salting-out of the enzyme, thereby to obtain the desired precipitates. The recovered precipitates may be purified, for instance, until they show a homogeneous protein bond in electrophoresis technique. The methods of purification is advantageously one which utilizes the characteristics of creatinase. For instance, the precipitates may be dissolved in a medium such as Tris-HCl buffer, and subjected to a chromatography by use of an anion-exchanging substance, such as diethylaminoethylcellulose, crosslinked diethylaminoethyldextran gel, crosslinked diethylaminoethylagarose gel, etc. or a gel-filtration agent, such as dextran gel and polyacrylamide gel. For example, a chromatography method with an anion exchanger of diethylaminoethylcellulose may be used to obtain a fraction eluted with 0.3 M KCl solution in concentration gradient of 0.1 to 0.5 M. According to the chromatography method by use of diethylaminoethyl cellulose, creatinase is eluted with 0.3 M KCl solution, while sarcosine oxidase is eluted with 0.36 M KCl solution. KCl concentration suitable for elution varies depending on the anion exchanging substance for chromatography employed. No doubt, the purification may be performed by a suitable combination of these procedures. Finally, purified powder containing only creatinase can be obtained by drying the product, for example, by lyophilization freeze drying process.

Figure 2:
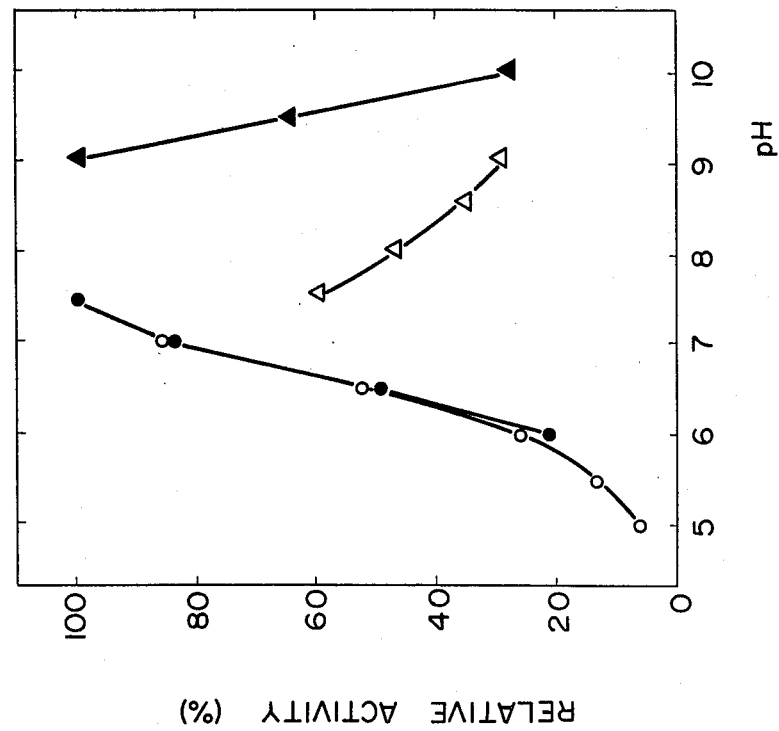
Figure 3:
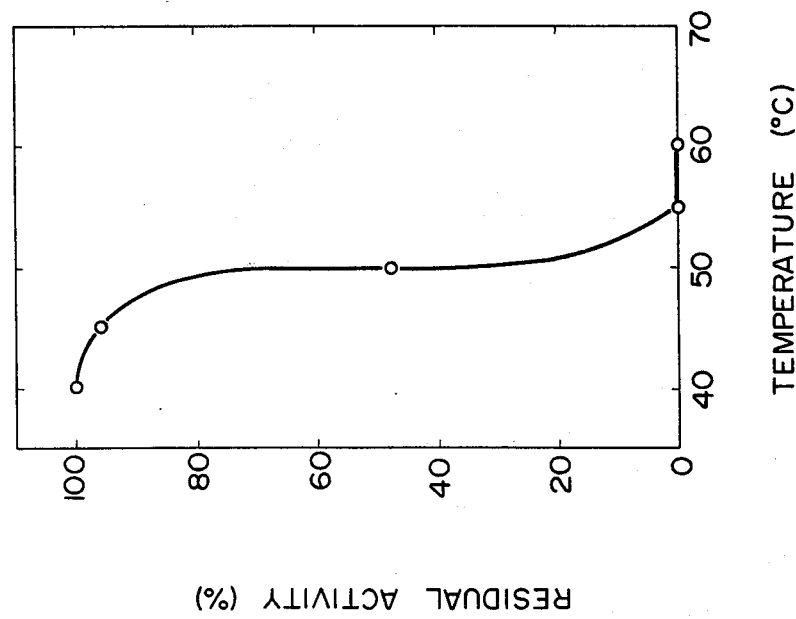

In the accompanying drawings,

FIG. 1 represents the optimum pH dependance of creatinase;

FIG. 2, pH stability of creatinase;

FIG. 3, thermal stability of creatinase; and

Figure 4:
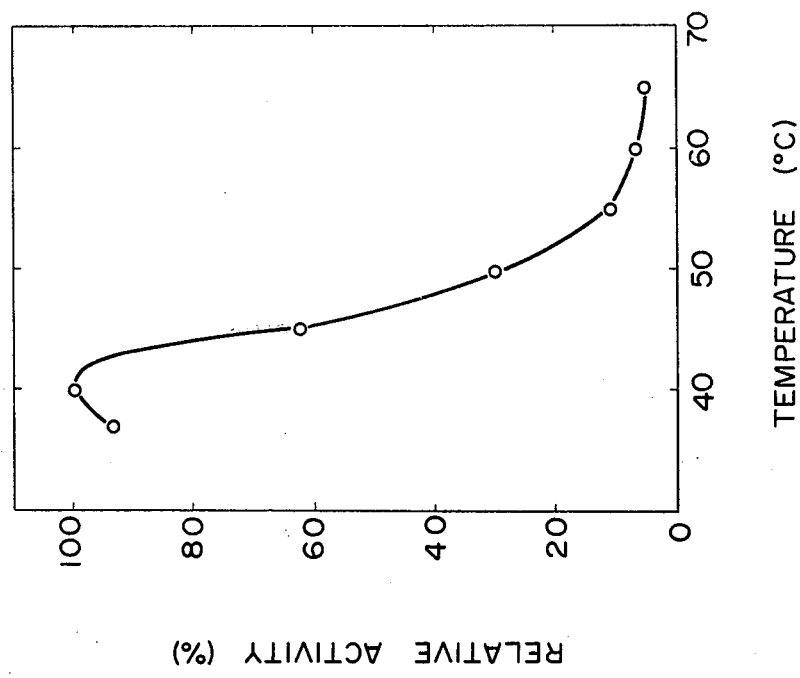

FIG. 4, the optimum temperature of creatinase activity.

Creatinase as obtained according to the present invention was assayed by the method of enzyme activity determination, and proved to have the physico-chemical properties, described below.

(1) Assay method of enzyme activity

Into 0.5 ml of a reaction mixture, consisting of 0.05 ml of 0.2 M phosphate buffer (pH 7.5) and 0.45 ml of 50 mM creatinase solution, is added 10 μl of enzyme solution, and the mixture is incubated at 37° C. for 5 minutes. Thereafter, the reaction is stopped by adding 0.5 ml of a 0.5 mM PCMB solution, and sarcosine formed by the reaction is determined by using sarcosine oxidase (E.C.1.5.3.1). Thus, 0.5 ml of a reagent solution, consisting of 0.1 ml of 0.2 M Tris-HCl buffer (pH 8.0), 0.05 ml of 0.3% 4-aminoantipyrine solution, 0.05 ml of 0.2% phenol solution, 0.05 ml of 0.05% (W/V) peroxidase solution, 0.1 ml of sarcosine oxidase solution (30 U/ml), and 0.15 ml of distilled water, is added to the reaction mixture as mentioned above, and the mixture is incubated at 37° C. for 20 minutes. After addition of 1.5 ml of distilled water, the reaction mixture is determined colorimetrically at 500 nm, to estimate the amount of the generated hydrogen peroxide, from which the amount of sarcosine formed by the action of creatinase is calculated.

One unit (1 U.) of the enzyme activity is defined as the amount of enzyme which forms 1μ mole of sarcosine from creatine at 37° C. per 1 minute.

(2) Reaction

The enzyme catalyzes the reaction which forms 1 mole of urea and sarcosine, from 1 mole of creatine with consumption of 1 mole of water.

(3) Optimum pH

The optimum pH of creatinase was found to be approximately 7.5-9.0. (Cf. FIG. 1)

The buffer solutions employed were dimethylglutarate-NaOH buffer (pH 5.0-7.0), phosphate buffer (pH 6.0-7.5), Tris-HCl buffer (pH 7.5-9.0), and glycine-NaOH buffer (pH 9.0-10.0), as shown in FIG. 1.

(4) pH stability

The enzyme was mixing with each of several buffers having different pH, incubated at 37° C. for 60 minutes, and thereafter assayed for residual activity. The buffers used were the same as described above. Creatinase is stable at about 6.0-9.0, as shown in FIG. 2.

(5) Thermal stability

Separate 1 ml fractions of creatinase solution in 10 mM phosphate buffer (pH 7.5) were subjected to various temperatures for 10 minutes, and assayed for the residual activity according to the assay method based on enzyme activity as described above. Creatinase proved to be stable at temperatures below approximately 40° C., as shown in FIG. 3.

(6) Optimum reaction temperature

The optimum reaction temperature of creatinase was formed to be approximately 40° C., as shown in FIG. 4.

(7) Molecular weight

About 74,000 (determined by gel filtration method).

(8) Isoelectric point

Around pH 4.9 (determined by isoelectric focusing electrophoresis, using a carrier ampholyte).

As mentioned heretofore, the enzyme, creatinase, of the present invention is recognized as an enzyme classified as creatine amidinohydrolase with the enzyme number of 3.5.3.3., from the fact that it reacts with creatine to form urea and sarcosine with consumption of water.

Creatinase of the invention can be utilized in various ways, including use as an enzymatic reagent for clinical diagnostics. For instance, it may be used for the determination of creatinine in serum or urine, in combination with creatininase and sarcosine oxidase, or it may be used for the assay of creatininase.

The following non-limiting examples are given by way of illustration only.

EXAMPLE 1

One hundred mililiters of a culture medium (pH 7.0), consisting of 0.5% of creatine, 0.5% of fish solubles, 0.2% of yeast extract, 0.3% of KCl, 0.1% of $K_2HPO_4$, and 0.05% of $MgSO_4.7H_2O$, were placed in a 500 ml volume Erlenmeyer flask, and sterilized at 120° C. for 20 minutes. The microorganism comprising the strain of Bacillus sp. B-0618, FERM-P No. 4049 was inoculated to the culture medium and cultivated at 30° C. for 1 day, thus obtaining a seed culture. Twenty liters of the culture medium having the same composition as described above was placed in a 30 l volume jar fermenter, and sterilized. After transplantation of the seed culture, the medium was cultivated under aeration-agitation at a temperature of 30° C. for 20 hours, with 200 r.p.m. stirring and 20 l/min. sterilized air rate. The resulting broth or cultivated product, was centrifuged to collect 12 g of wet cells, which were rinsed with a 10 mM phosphate buffer (pH 7.0), suspended in the same buffer, put with lysozyme (final concentration=0.2 mg/ml), incubated at 37° C. for 30 minutes, and centrifuged at 5,000 r.p.m. for 15 minutes, to obtain the supernatant (the enzyme activity as sarcosine oxidase, 1400 U and the enzyme activity as creatinase, 800 U). The resulting supernatant was mixed with 2.5 ml of an aqueous 2% protamine sulfate solution and centrifuged to remove nucleic acids. Then, the solution was treated with a saturated ammonium sulfate solution, and the precipitates settling at the fractions of from 50% to 70% concentration of ammonium sulfate, were separated and dissolved into 20 ml of 10 mM Tris-HCl buffer (pH 8.0). The fractionation with ammonium sulfate solution was repeated twice, and the precipitates were dissolved into 10 mM Tris-HCl buffer (pH 8.0). The resulting solution was desalted by passing through a column (3.5 cm diameter×30 cm) filled with dextran gel ("Cephadex G-25," made by Pharmacia), and charged into diethyl-aminoethyl ("DEAE-cellulose" made by Brown) column (2.0 cm diameter×18 cm), which had been equilibrated with 10 mM Tris-HCl buffer (pH 8.0). After washing with the same buffer containing 0.1 M KCl, the enzyme was eluted with aqueous KCl solutions in concentration gradient of 0.1 M to 0.5 M. The active fraction eluted with 0.3 M KCl solution and the active fraction eluted with 0.36 M KCl solution were separately recovered and the active fraction eluted with 0.3 M KCl solution was concentrated by a ultrafilter (made by Amicon), dialyzed for 10 hours against a 10 mM phosphate buffer (pH 7.5), and then lyophilized, thus obtaining creatinase powder (220 U of total activity, 38 mg of protein, 5.8 U/mg of specific activity, and 27.5% of recovery; sarcosine oxidase activity was not detected).

The active fraction eluted with 0.36 M KCl solution was dialyzed for 10 hours against a 10 mM Tris-HCl buffer (pH 8.0) by a dialysis membrane (Visking Co.) and then was freezedried to obtain sarcosine oxidase powder (540 U of total activity, 43 mg of protein, 12.7 U/mg of specific activity and 38.6% of recovery; creatinase activity was not detected.)

EXAMPLE 2

One hundred mililiters of a culture medium (pH 7.2) consisting of 1.5% creatine, 0.5% of peptone, 0.2% of yeast extract, 0.5% of corn steep liquor, 0.1% of KCl, 0.1% of $K_2HPO_4$ and 0.05% of $MgSO_4.7H_2O$ were placed in a 500 ml volume Erlenmeyer flask, and sterilized at 120° C. for 20 minutes. Then, Bacillus sp. B-0618 (FERM-P No. 4049) was inoculated to the culture medium and cultivated at 30° C. for 1 day to obtain a seed culture. Twenty liters of the culture medium having the same composition as that described above were placed in a 30 l volume jar fermenter and sterilized. After transplantation of the seed culture, the medium was cultivated under aeration-agitation at a temperature of 30° C. for 18 hours at 300 r.p.m. and 20 l/min. sterilized air flow rate. The resulting cultivated product was centrifuged to obtain 230 g of wet cells. Then, 230 g of the wet cells were suspended in 3 l of 20 mM phosphate buffer (pH 8.0) containing lysozyme (0.5 mg/ml) and EDTA (2 mM) and the suspension was allowed to react for 1.5 hours at 37° C. under agitation. The suspension was centrifuged at 5,000 r.p.m. for 15 minutes to recover a supernatant (2.85 l, 24,300 U). To the resulting supernatant was added 28.5 ml of a 2% aqueous solution of protamine sulfate and the mixture was centrifuged (5,000 r.p.m., 15 minutes) to obtain a supernatant (2,830 ml, 24,050 U), which was concentrated under reduced pressure (800 ml, 23,600 U). Further, 320 ml of a saturated ammonium sulfate solution was added to this and the resulting solution was centrifuged at 10,000 r.p.m. for 10 minutes to obtain a supernatant. To this supernatant was added 220 ml of the saturated ammonium sulfate solution. The mixture was centrifuged at 10,000 r.p.m. for 10 minutes to recover precipitates. The precipitates were dissolved in 200 ml of 20 mM phosphate buffer having a pH of 8.0 and the insolubles removed by centrifugation to obtain a supernatant (195 ml, 17,600 U). After the supernatant was further concentrated by ultra filtration (80 ml, 17,400 U), the resulting slution was dialyzed against a 10 mM phosphate buffer (pH 8.0). The solution was charged into diethylaminoethyl agarose ("DEAE-sepharose CL-6B") column (5.0×60 cm) which had been equilibrated with a 10 mM Tris-HCl buffer (pH 8.0). After washing with 2 l of the same buffer containing 0.2 M KCl, the enzyme was eluted with buffers (1.5 l, respectively) containing 0.2 to 0.5 M KCl according to the concentration gradient method, and the active fraction eluted with 0.35-0.37 M KCl was collected (380 ml, 13,500 U). It was concentrated by ultra filtration (40 ml, 13,400 U). The concentrate was charged into acrylamide gel ("Biogel P-2") column for desalting to obtain 90 m l of an eluate (12,500 U). To this was then added 1.8 ml of a 50% sucrose solution and the resulting mixture was lyophilized to obtain 1,265 mg of creatinase powder (specific activity: 8.2 U/mg, recovery: 42.7%).

What we claim is:

1. A method for producing and isolating creatinase which comprises culturing a creatinase producing microorganism Bacillus sp. B-0618, Firm-P No. 4049, fractionally eluting sarcosine oxidase and creatinase by anion exchange chromatography from the sarcosine oxidase- and creatinase-containing solution thus produced to obtain a creatinase eluted fraction and collecting creatinase therefrom.

2. A method according to claim 1 wherein the anion exchange chromatography medium is diethylaminoethyl cellulose and the creatinase eluted fraction is eluted with 0.3 M KCl solution in concentration gradient of KCl 0.1 M to 0.5 M.

3. A method according to claim 1 wherein the anion exchange chromatography medium is diethylaminoethyl cellulose and the creatinase eluted fraction is eluted with 0.2-0.5 M KCl solution in concentration gradient of KCl 0.35-0.37 M.

* * * * *